United States Patent [19]

Hodgen

[11] Patent Number: 5,468,736
[45] Date of Patent: Nov. 21, 1995

[54] HORMONE REPLACEMENT THERAPY

[75] Inventor: Gary D. Hodgen, Norfolk, Va.

[73] Assignee: The Medical College of Hampton Road, Norfolk, Va.

[21] Appl. No.: 23,692

[22] Filed: Feb. 25, 1993

[51] Int. Cl.$^6$ .................................................. A61K 31/56
[52] U.S. Cl. ......................................... 514/179; 514/170
[58] Field of Search ......................................... 514/170, 179

[56] References Cited

U.S. PATENT DOCUMENTS

| | | | |
|---|---|---|---|
| 3,890,356 | 6/1975 | Grunwell et al. | 260/397.5 |
| 3,928,398 | 12/1975 | Grunwell et al. | 260/397.5 |
| 4,416,822 | 11/1983 | Campbell | 260/397.4 |
| 4,670,426 | 6/1987 | Zor et al. | 514/171 |

FOREIGN PATENT DOCUMENTS 145493  6/1985  European Pat. Off. .

OTHER PUBLICATIONS

CA 111(15): 127206n, Van Uern et al., 1989.
Conn's Current Therapy, Menopause, Wulf H, Utian, pp. 1017–1020, 1992.
Barbieri et al., A Clinician's Dilemma, HRT and Breast Cancer Risk, Menopause Management, Jul./Aug. 1992, 12–24.
J. F. H. M. van Uem,, M.D., Contraceptive Potential of RU 486 by Ovulation Inhibition: I. Pituitary Versus Ovarian Action with Blockade of Estrogen–Induced Endometrial Proliferation, Aug. 1989, vol. 40, No. 2, pp. 171–184.
K. A. Steingold, M.D. et al., Antiprogestins in Reproductive Medicine, Sex Steroids, vol. 3, No. 1, Jan. 1992, pp. 233–249.
G. D. Hodgen, PhD., Progesterone Antagonists: Useful for Contraception?, Contemporary OB/GYN Special Issue, pp. 65 and 66, (1988).
Sheth et al., A Randomized, Double–Blind Study of Two Combined and Two Progestogen–Only Oral Contraceptives, Contraception, 25:243, 1982.
Collins et al., Blockade of the spontaneous midcycle gonadotropin surge in monkeys by RU 486, J Clin Endocrinol Metab. 63:1270, 1986.
Danforth et al., Contraceptive Potential of RU 486 By Ovulation Inhibition III Preliminary Observations on Once Weekly Oral Administration, Contraception, 40:195, 1989.
Shoupe et al., Effects of an antiprogenterone RU 486 in normal women II: administration in the late follicular phase, Am J Obstet Gnyecol, 157:1421, 1987.

Liu et al., Disruption of follicular maturation and delay of ovulation after administration of the antiprogesterone Ru 486, J Clin Endocrinol Metab, 65:1135, 1987.
Luukkainen et al., Inhibition of folliculogenesis and ovulation by the antigesterone RU 486, Fert Steril, 49:961, 1988.
Batista et al., delayed endometrial matuaration induced by daily administration of antiprogestin RU 486: A patential new contraceptive strategy, Am J Obstet Gynecol, 167:60, 1992.
Messinis et al., The Effect of the Antiprogestin Mifepristone RU–486 On Maturion and In–Vitro Fertilization of Human Ooxytes, Br J Obstet Gynecol, 95(6), 1988–Abstract.
Juneja et al., In Vitro Effect of RU 486 On Sperm–Egg Interaction in Mice, Am J Obstet Gynecol, 163:216, 1990.
Chwalisz et al., Inhibition of Estradiol–Mediated Endometrial Gland Formation by the Antigestagen Onapristone In Rabbits: Relationship to Uterine Estrogen Receptors, Endocrinology 129:312, 1991–Abstract.
Anon., Research Disclosure 28976, 1992.
Hodgen, Surrogate Embryo Transfer Combined with Estrogen–Progesterone Therapy In Monkeys, JAMA 250:2167, 1983.
Chillik et al., Characterizing Pituitary Response to Gonadotropin–releasing Hormone (GnRH) Antagonist in Monkeys: Tonic Follicle–stimulating Hormone/luteinizing Hormone Secretion Versus Acute GnRH Challenge Tests Before, During and After Treatment, Fert. Sterol, 48:480, 1987.
Yoshimura et al., Progesterone Protects Oocytes from Premature Degeneration within the Follicle, Nippon Sanka Fujinka Gakkai Zasshi, 42(9):1256, 1990–Abstract.
Sakiz et al. R 2323–An Original Contraceptive Compound, Excerpta Medica, Abs. 86, 1970.
Spitz, Clinical Applications of the Antiprogestin RU 486, The Endocrinologist, 3:58, 1993.
Gravanis et al., Endometrial and Pituitary Responses to the Steroidal Antiprogestin RU 486 in Postmenopausal Women, J. Endocrinol. Metab. 60:156, 1986.
Wolf et al., Noncompetitive Antiestrogenic Effect of RU 486 in Blocking the Estrogen Stimulated Luteinizing Hormone Surge and the Proliferative Action of Estradiol on Endometrium in Castrate Monkeys, Fert. Steril., 52:1055, 1989.

*Primary Examiner*—Kimberly R. Jordan
*Attorney, Agent, or Firm*—Ostrolenk, Faber, Gerb & Soffen

[57] ABSTRACT

A method of hormone replacement therapy involves the administration of estrogen together with an amount of antiprogestin which inhibits estrogen-induced endometrial proliferation in a woman.

20 Claims, 1 Drawing Sheet

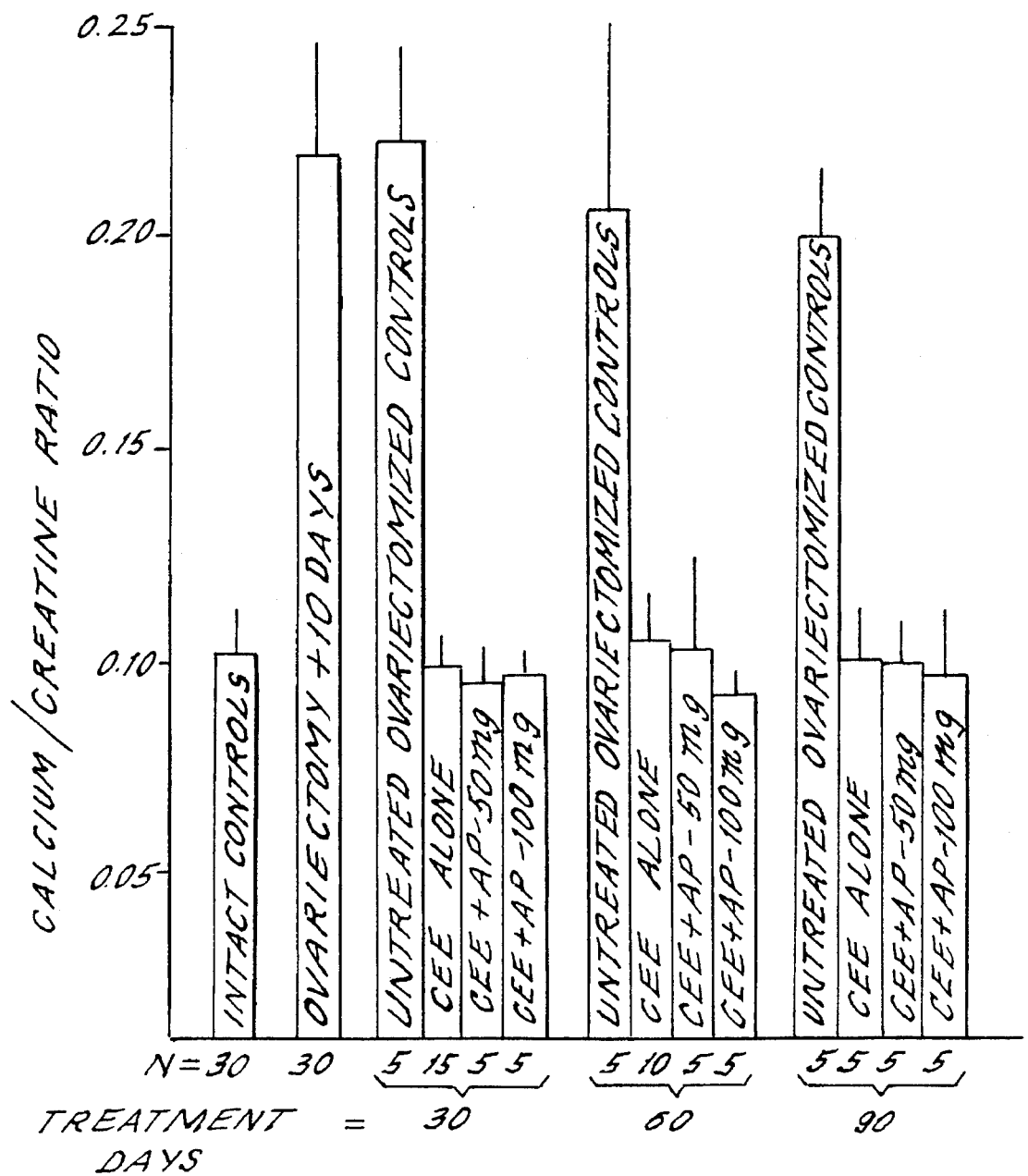

HORMONE REPLACEMENT THERAPY

BACKGROUND OF THE INVENTION

More than 40 million women in the United States alone have entered their post-menopausal years. The life expectancy of a woman who has attained her last menstrual period is about 28 years and a study in 1982 indicated that about 75 to 85% of these women will develop symptoms of estrogen deficiency (Hammond et al., *Fertilo Steril.* 37(1): 5–25, 1982). One of the most common complaints of women following the commencement of ovarian failure is the "hot flash" or vasomotor symptom complex. This is characterized by a sudden onset of warmth generally lasting a few minutes, frequently evidenced by a visible red flush, and often accompanied by dizziness, nausea, headache, palpitations and diaphoresis. Adequate estrogen supplementation has been shown to provide relief to over 90% of these individuals.

There are many other post-menopausal symptoms of chronic hypoestrogenism, among the most serious is osteoporosis and ischemic heart disease. As many as 25% of women over 60 years old have documented spinal compression fractures as a result of osteoporosis related to estrogen deficiency and as many as 50% develop vertebral fractures by age 75° A very large percentage of hip fractures in the elderly are attributable to osteoporosis. In 1980, a study carried out at the Mayo Clinic calculated the cost of hospital stays due to fractures at over one billion dollars per year (Gallagher et al., *Clin. Ortho.*, 150:163, 1980).

Long-term estrogen replacement therapy is common for post-menopausal and other estrogen deficient women. It is, however, a more complicated issue for women having a uterus. Estrogen therapy has been associated with an increased incidence of endometrial cancer due to the continual "unopposed" estrogen-induced proliferation of the endometrium. Regular progestin administration inhibits the continual estrogen stimulation of the endometrium through an anti-proliferative effect and seems to reduce the rate of endometrial carcinoma in post-menopausal women receiving estrogen by several fold (Barbieri et al., *Menopause Management*, July/August 1992, 12–24). However, combination of estrogen and progestin frequently causes undesirable uterine bleeding which reduces the rate of patient compliance. There is also concern that the cardiovascular benefits of estrogen might be minimized by progestins (Speroff, *Current Trends in Estrogen Replacement Therapy*, 1986), Nevertheless, both sequential and concurrent estrogen plus progestin regimens are now predominately used in hormone replacement therapy for menopausal women with a uterus° Notwithstanding the above, a woman without a uterus is adequately treated by estrogen alone.

Despite the well-established overall benefits of estrogen plus progestin replacement therapy for women having a uterus, the rate of patient compliance with this therapy suffers markedly because the treatment often requires women to endure side effects such as unpredictable bleeding and cyclotherapeutic withdrawal menstrual bleeding during a time in their lives when many women welcome cessation of menstrual bleeding as a normal occurance in menopause° These side effects can be experienced during the entire treatment interval, which could be for the remainder of life. User satisfaction and compliance should all increase greatly if the principal benefits of the estrogen replacement therapy could be maintained while the estrogen-induced endometrial proliferation is inhibited without uterine bleeding.

The nature of the invention described here stems from the antiproliferative action of antiprogestin, i.e., its ability to inhibit endometrial proliferation during hormonal replacement therapy. This antiproliferative effect by antiprogestins per se has been noted (Gravanis et al., *J Clin Endocrinol Metab*, 60: 156, 1986; Wolf et al., *Fertil Steril*, 52:1055, 1989; Chualisz et al., *Endocrinology*, 129: 312, 1991), but the therapeutic value of this effect for hormone replacement therapy to menopausal women (which extends over a minimum interval of 20 days) has not been previously recognized.

The absence of thickening (proliferating) endometrium, as can be achieved with the administration of antiprogestins during extended estrogen replacement therapy, would decrease the risk of endometrial carcinoma (which is also decreased with progestins), but unlike that obtained with progestins would avoid unwanted vaginal bleeding that markedly reduces therapy compliance among postmenopausal women. Moreover, the addition of estrogen in combination with antiprogestin provides this advantage without negating the bone conserving efficacy derived from estrogen replacement therapy. These therapeutic advantages are achieved without any complications that accompany progestin administrations which in this invention is excluded in its entirety.

It is accordingly the object of this invention to provide a method of inhibiting the estrogen-induced proliferation of the endometrium without undesirable uterine bleeding and without sacrificing the advantageous properties of estrogen replacement therapy. This and other objects of the invention will become apparent to those of ordinary skill in the art from the following detailed description.

SUMMARY OF THE INVENTION

This invention broadly relates to a method of hormone replacement therapy. More particularly, it relates to a method of hormone replacement therapy in which an estrogen replacement therapy effective amount of estrogen is administered to women in need of such therapy and, in addition, antiprogestin is also administered in an amount which inhibits estrogen-induced endometrial proliferation, thus avoiding uterine bleeding.

BRIEF DESCRIPTION OF THE DRAWING

The FIGURE shows the dependency of the urinary calcium/creatinine ratio on estrogen.

DETAILED DESCRIPTION OF THE INVENTION

In accordance with the present invention, a hormone replacement therapy is provided employing an estrogen together with the co-administration of an amount of antiprogestin which inhibits estrogen-induced endometrial proliferation.

The estrogen aspect of the invention is analogous to conventional estrogen replacement therapy. Accordingly, any known estrogen material, dosage amount and method heretofor employed in the usual estrogen replacement therapy can be employed in the practice of the present invention. Examples of estrogens which can be employed are ethinyl estradiol and estradiol and their esters such as the acetate, valerate or benzoate, mestranol and conjugated equine estrogens. The estrogen is administered in the conventional manner by any route where it is active, for instance orally or transdermally. Most estrogens are orally active and that route of administration is therefore preferred. Accordingly, administration forms can be tablets, dragees, capsules or pills which contain the estrogen and a suitable pharmaceutically acceptable carrier.

For example, the amount of conjugated equine estrogen administered is analogous to that practiced in conventional estrogen replacement therapy and is generally in the range of about 0.3 to 1.2 mg, preferably about 0.625 to 0.9 mg daily. The determination of an effective dose is a routine exercise in the pharmaceutical arts, taking into account such various physical parameters as weight, age and the like, and is best determined by the attending clinician. The administration can be periodic, such as on a weekly basis, or continuous such as on a daily basis. The latter, that is daily administration, is preferred because individuals are more likely to follow the treatment regiment and not to forget or overlook a periodic administration schedule.

The antiprogestin can be a progesterone receptor antagonist or a pharmaceutically suitable agent that counteracts the normal biological activity of progesterone. A preferred antiprogestin is a progesterone receptor antagonist. For example, RU 486 is particularly suitable in the practice of this invention.

Examples of antiprogestins which can be employed in this invention are RU 486 ("mifepristone", Roussel Uclaf, Paris; U.S. Pat. No. 4,386,085); and "onapristone" (Schering Ag, Berlin; U.S. Pat. No. 4,780,461) and the steroids described in the following patents and patent applications: U.S. Pat. No. 4,609,651, especially the compound lilopristone (11β-(4-dimethylaminophenyl)- 17β-hydroxy-17α-(3-hydroxy-prop-1-(Z)-enzyl- 4,9(10) estradien-3-one); U.S. application Ser. No. 06/827,050, especially the compounds acetylphenyl)-17β-hydroxy-17α-(1-propinyl)-4,9-estradien- 3-one and 11β-(4-acetylphenyl)-17β-hydroxy-17α-(3-hydroxy-1(2)-propenyl)-4,9-estradien-3-one; U.S. application Ser. No. 07/283,632; published European patent application EP-A 04042831; and other anti-progestins, e.g., U.S. Pat. No. 4,891,368.

The antiprogestin can be administered by way of any art recognized means as practiced in the pharmaceutical arts. For example, a suitable antiprogestin may be so formulated so that it can be administered orally, via a skin patch for transdermal absorption, contained within an inert matrix which is implanted within the body and in the depot state or intravaginally in a matrix that slowly releases the antiprogestin (such an implant is taught in U.S. Pat. Nos. 4,957,119 and 5,088,505 and the like).

Pharmaceutical formulations containing the antiprogestin and a suitable carrier can be solid dosage forms which includes tablets, capsules, cachets, pellets, pills, powders or granules; topical dosage forms which includes solutions, powders, fluid emulsions, fluid suspensions, semi-solids, ointments, pastes, creams, gels or jellies and foams; and parenteral dosage forms which includes solutions, suspensions, emulsions or dry powder comprising an effective amount of antiprogestin as taught in this invention. It is known in the art that the active ingredient, the antiprogestin, can be contained in such formulations in addition to pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, "Modern Pharmaceutics", Banker & Rhodes, Marcel Dekker, Inc. 1979; "Goodman & Gilman's The Pharmaceutical Basis of Therapeutics", 6th Edition, MacMillan Publishing Co., New York 1980 can be consulted.

The estrogen and antiprogestin components of the hormone replacement therapy methods of the invention can be co-administered utilizing the same or different dosage forms or means, for example the same tablet, or the estrogen component may be provided continuously by implant or depot with supplemental amounts of antiprogestin provided orally on a periodic basis. Application of the components, compositions and methods of the present invention for the medical or pharmaceutical uses described herein can thus be accomplished by any clinical, medical or pharmaceutical methods and techniques as are presently or prospectively known to those skilled in the art.

The pharmaceutical formulations may be provided in kit form containing a plurality of, generally at least about 20, and preferably in multiples of 7 such as 28, tablets, intended for ingestion on successive days. Where administration of the antiprogestin is intended to be periodic, a plurality, generally at least three, of non-adjacent tablets contain the antiprogestin while the remaining tablets are placebo. Where convenient, the kit may provide the estrogen and antiprogestin can be in the same tablet.

The administration of the antiprogestin is in an amount which inhibits estrogenic endometrial proliferation. This is generally about 0.005 to 1 mg/kg, and preferably about 0.05 to 0.5 mg/kg, daily in the case of RU 486. Other milligram amounts may be appropriate in the case of different antiprogestins. Regimens of estrogen and antiprogestin other than daily and/or in which the dosage amount of the estrogen and antiprogestin is periodically varied are also within the scope of the invention. It should also be appreciated that a minor amount of periodic bleeding or spotting on a monthly or yearly basis can occur. In other words, the amenorrhea state (the absence of menstrual-like bleeding) established in this invention is substantially, but not necessarily totally, complete. The appropriate amount of the antiprogestin in the practice of the present invention can, as with the estrogen amount, be determined by using art recognized methods, for example by establishing dose-response curves in suitable primate models and extrapolating to humans, extrapolating from suitable in vitro systems or determining effectiveness in clinical trials. The attending clinician will, as in the case of the estrogen, take weight, age and other physical and medical parameters into account when establishing an appropriate dosage amount.

The administration of the antiprogestin can either be periodic such as on a weekly basis or continuous, that is on a daily basis. A daily administration is preferred because individuals are more likely to follow the treatment regimen and not to forget or overlook a periodic administration schedule. In the case of the antiprogestin RU 486, a suitable human oral dose will be on the order of about 0.5 to 10 mg per dose, preferably about 1 to 5 mg per dose daily. This amount can be lowered or raised based on the administration regimen and based on the characteristics of the individual receiving the treatment. Variations of dosage based on the route of administration may vary and such changes can be determined practicing known techniques.

In order to further illustrate the present invention, specific examples are set forth below. It will be appreciated, however, that these examples are illustrative only and are not intended to limit the scope of the invention.

EXAMPLE 1

For the purposes of this study, the antiprogestin selected was RU 486 and this was administered to female monkeys, which are recognized to be a suitable model for human research.

Thirty adult females cynomolgus monkeys (*Macaca fascicularis*) weighing 3.1 to 5.2 kg and having presumably ovulatory, regular menstrual cycles were housed in individual cages which had food and water available at libitum, except when urine was collected. These collections were made after overnight fasting with provision of distilled drinking water in order to avoid contamination with food and/or fecal matter. Detection of blood in the vagina was accomplished by daily vaginal swabs between 6 and 9 A.M. using a saline moistened cotton-tipped applicator. Blood and urine specimens were obtained at the commencement of the study, 10 days after surgical bilateral ovariectomy, 30 days after initiation of treatment, 60 days after initiation of treatment and 90 days after initiation of treatment.

The monkeys were randomly assigned to four groups. Five monkeys were in group I and these constituted ovariectomize controls. Group II consisted of fifteen monkeys which were treated with 0.15 mg conjugated equine estrogens (hereinafter CEE) orally per day. Group II was subdivided into three groups of five animals each, and the subgroups were treated for 30; 60 or 90 days, respectively. Group III consisted of five monkeys which were treated with 0.15 mg CEE orally per day and also administered 0.5 mg of the antiprogestin RU 486 orally per day for 90 days. Group IV consisted of five monkeys which were treated in the same way as Group III except that the dosage of RU 486 was 10 mg. All medications were administered by garage between 6 and 9 A.M.

Table 1 below summarizes the incidents of bleeding, either withdrawal menses or breakthrough bleeding, among the treatment groups.

inconsequential in all groups. The additional administration of the antiprogestin at both dosages markedly curtailed bleeding of any kind and except for a few episodes of spottings a state approaching amenorrhea was sustained in the two weeks after the treatment ended. This was particularly evident at the higher dosage level. The lack of withdrawal bleeding was statistically significantly different.

The data set forth in the FIGURE demonstrates the acute dependency of the urinary calcium/creatinine ratio on an adequate physiologic supply of estrogen. The CEE dosage employed was fully sufficient to restore this metabolic marker to near pretreatment levels at 30, 60 and 90 days. Importantly, addition of the antiprogestin to achieve an atrophic endometrial status and amenorrhea did not deter the acute beneficial effects of the estrogen therapy. A consistent trend, albeit not statistically significant, shows the RU 486 may have lowered the calcium/creatinine ratio even more than CEE alone.

The data obtained during the study confirms that the antiprogestin used in the combination with the estrogen in the hormone replacement therapy regimen was highly advantageous. It showed an avoidance of menses induced by cyclic therapeutic regimens, without sacrificing the protective actions of estrogen therapy on acute calcium homeostasis as assessed by urinary excretion. In like manners these data suggest that benefit of estrogen can be retained within the range of antiprogestin dosage which attains amenorrhea without compromising the beneficial effects of estrogen on proliferal actions of the body, including: coronary vessels, vaginal tissues, temperature regulation of the hypothalamus, determatological effects, mood effects and the like. The antiprogestin may counter the known association between estrogen therapy and breast cancer risk in that the administration of the antiprogestin may counteract estrogen-dependant tumor growth and/or progestin-dependant tumor growth.

| Endometrial Status During Conjugated Equine Estrogen Treatment, with and Without Antiprogestin Therapy in Ovariation Primates[1]: Withdrawal Menses and Breakthrough Bleeding As An Indication of Proliferative Versus Atrophic Tissue | | | | | | |
|---|---|---|---|---|---|---|
| Monkey Groups | N | Treatment Internal (Days) | Incidents of Breakthrough Bleeding[4] (Days) | Withdrawal Menses[4] Range of | | Duration of Withdrawal Bleeding[4] |
| | | | | Individuals | Days Detected | Days; x + SEM |
| I. Untreated Controls | 5 | — | 0 | 0/5 | — | — |
| II. CEE[2] 0.15 mg Alone | 5 | 30 | 0 | 5/5 | 32 to 44 | 5.2 ± 4.4 |
| | 5 | 60 | 3 | 5/5 | 63 to 71 | 6.6 ± 3.7 |
| | 5 | 90 | 2 | 5/5 | 92 to 103 | 6.4 ± 4.5 |
| III. CEE[2] 0.15 mg + AP[3] 5.0 mg | 5 | 90 | 0 | 3/5 | one day 94 and 96 one day 93 only one day 96 only | <1[5] |
| IV. CEE[2] 0.15 mg + AP[3] 10.0 mg | 5 | 90 | 2 | 1/5 | day 95 only | <1[5] |

[1]Cynomolgus monkeys were ovariectomized 10 days before initiation of treatments.
[2]Conjugated equine estrogens (CEE), orally administered daily
[3]Antiprogestin (AP), RU486 orally administered daily.
[4]Blood in the vagina was detected by daily swabs.
[5]Significantly reduced withdrawl bleeding ($P < 0.005$)

The administration of the estrogen alone uniformly led to withdrawal bleeding regardless of the length of the treatment and the duration of the bleeding was highly individualized, averaging from 5 to 6 days, although the onset and cessation were spread over almost two weeks after ending the CEE administration. Breakthrough bleeding was negligible and

EXAMPLES 2–9

Following the procedures set forth in Example 1, hormone replacement study is repeated with the following combination of agents:

| Example | Estrogen | Antiprogestin |
| --- | --- | --- |
| 2 | estriol (E3) | onapristone |
| 3 | estetrol (E4) | lilopristone |
| 4 | estradiol | 11β-(4-acetyl-phenyl)-17β-hydroxy-17α-(1-propinyl)-4,9-estradien-3-one |
| 5 | estrone | 11β-(4-acetyl-phenyl)-17β-hydroxy-17α-(3-hydroxy-1(2)-propenyl)-4,9-estradien-3-one |
| 6 | estrone sulfate | mifepristone |
| 7 | ethinyl estradiol | onapristone |
| 8 | estropipate | lilopristone |
| 9 | 11-nitro estradiol | mifepristone |

Various changes and modifications can be made in the present invention without departing from the spirit and scope thereof. The various embodiments which have been described and illustrated herein were intended to be representative and not limiting.

What is claimed is:

1. A method of hormone replacement therapy which comprises administering to a woman in need of such therapy, estrogen in an hormone replacement therapy effective amount and antiprogestin in an amount which is effective both to inhibit estrogen-induced endometrial proliferation and to effect a state of .substantial amenorrhea, in the absence of progestin administration.

2. The method of claim 1 in which the antiprogestin is administered daily.

3. The method of claim 2 in which the administration is oral.

4. The method of claim 1 in which the estrogen and antiprogestin are administered daily.

5. The administration of claim 1 in which the administration is oral.

6. The method of claim 1 in which each administration contains about 0.5 to 10 mg of the antiprogestin daily.

7. The method of claim 6 in which the amount is about 1 to 5 mg.

8. The method of claim 1 in which the mode of administration is by depot.

9. The method of claim 1 in which the antiprogestin is a progestin receptor antagonist.

10. The method of claim 9 in which the antiprogestin is RU 486.

11. The method of claim 1 in which the administration extends over a minimum interval of 20 days.

12. In a method of hormone replacement therapy in which estrogen is administered in the absence of progestin administration to a woman in need of such therapy, the improvement which comprises the additional administration to said woman of antiprogestin in an amount which both inhibits estrogen-induced endometrial proliferation and effects a state of substantial amenorrhea.

13. A kit containing at least 20 tablets, a portion of which contain a hormone replacement therapy effective amount of an estrogen and at least 20 of which contain an amount of an antiprogestin which both inhibits estrogen-induced endometrial proliferation and effects a state of substantial amenorrhea.

14. The kit of claim 13 in which each tablet contains both the estrogen and antiprogestin.

15. The kit of claim 14 in which the amount of antiprogestin is about 0.5 to 10 mg.

16. The kit of claim 15 in which the amount of antiprogestin is about 1 to 5 mg.

17. The kit of claim 16 in which the antiprogestin is RU 486.

18. The kit of claim 13 in which the amount of antiprogestin is about 0.5 to 10 mg.

19. The kit of claim 13 in which the amount of antiprogestin is about 1 to 5 mg.

20. The kit of claim 13 in which the antiprogestin is a progestin receptor antagonist.

\* \* \* \* \*